United States Patent [19]

Sircar et al.

[11] Patent Number: 4,717,730

[45] Date of Patent: Jan. 5, 1988

[54] 4,5-DIHYDRO-6-(SUBSTITUTED)PHENYL-5-METHYL-3-(2H)-PYRIDAZINONES AND PHARMACEUTICAL COMPOSITIONS CONTAINING THE COMPOUNDS AS ACTIVE COMPONENTS

[75] Inventors: Ila Sircar; James A. Bristol, both of Ann Arbor, Mich.

[73] Assignee: Warner-Lambert Company, Morris Plains, N.J.

[21] Appl. No.: 446,797

[22] Filed: Dec. 3, 1982

[51] Int. Cl.$^4$ .................... C07D 403/10; A61K 31/50
[52] U.S. Cl. .................................. 514/252; 514/247; 544/238; 544/239
[58] Field of Search ................ 544/238, 239; 424/250; 514/247, 252

[56] References Cited

U.S. PATENT DOCUMENTS 4,353,905  10/1982  Sircar et al. ........................ 544/239
4,361,563  11/1982  Austel et al. ....................... 544/238

Primary Examiner—Nicholas S. Rizzo
Attorney, Agent, or Firm—Jerry F. Janssen

[57] ABSTRACT

A novel method of producing 4,5-dihydro-6-(substituted)phenyl-5-methyl-3(2H)-pyridazinone compounds and the corresponding pharmaceutically acceptable salt compounds is provided as well as pharmaceutical compositions containing one or more of the compounds as active components of the compositions for their pharmacological activity, particularly their cardiotonic and/or antihypertensive activity.

Said 5-methylpyridazinone compounds have greatly improved cardiotonic activity in vivo that causes, for example, a significant increase in myocardial contractility in the dog. Said compounds also cause a decrease in blood pressure in the spontaneously hypertensive rat. Said compounds are produced by a stepwise procedure in which one reacts a substituted morpholineacetonitrile with crotononitrile to obtain the corresponding 4-(substituted)-$\beta$-methyl-$\gamma$-oxobenzenebutanoic acid and reacts the latter acid with hydrazine to provide the 4,5-dihydro-6-(substituted)phenyl-5-methyl-3(2,uns/H/)-pyridazinone product.

2 Claims, No Drawings

4,5-DIHYDRO-6-(SUBSTITUTED)PHENYL-5-METHYL-3-(2H)-PYRIDAZINONES AND PHARMACEUTICAL COMPOSITIONS CONTAINING THE COMPOUNDS AS ACTIVE COMPONENTS

BACKGROUND OF THE INVENTION 4,5-Dihydro-6-(substituted)phenyl-3(2H)-pyridazinone compounds that are useful as cardiotonic agents and antihypertensive agents are known from our U.S. Pat. No. 4,353,905, issued Oct. 12, 1982. It is also known from J. D. Albright, F. McEvoy and Daniel B. Moran (J. Het. Chem., 15, 881 (1978) to prepare a 4-substituted-β-methyl-γ-oxobenzenebutanoic acid from a 4-substituted benzaldehyde.

SUMMARY OF THE INVENTION

The present invention relates to a novel method of producing compounds of a unique subgroup of such compounds having the structural formula (I):

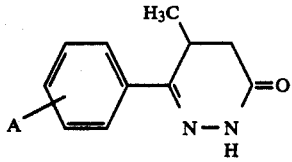

wherein A is any of the imidazolyl, imidazolylalkyl, imidazolylalkyloxy, pyrrolyl and triazolyl groups attached to the 3- or 4-position of the phenyl ring having the structural formula:

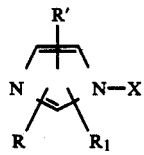

wherein $R_1$, $R'$, and R are independently hydrogen or lower alkyl, $CH_2OH$, $SCH_3$, $SOCH_3$, $SO_2CH_3$, hydroxyalkyl, halogen, $(CH_2)_k NR''R'''$ wherein k is 0 to 2 and $R''$ and $R'''$ are independently hydrogen or lower alkyl, wherein lower alkyl contains one to six carbon atoms; or, when attached to the 4- and 5-positions of the imidazole ring, may be taken together to form a (i) 5-, 6-, or 7-membered ring which may also contain a nitrogen atom, (ii) benzene ring which is optionally substituted by halogen, hydroxy, lower alkyl, and lower alkyloxy, and (iii) pyridine ring; X is a bond, $(CH_2)_n$ or $O(CH_2)_{n+1}$ wherein n is 1 to 4; or the structural formula:

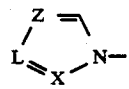

wherein
(i) X=L=Z=CH
(ii) X=Z=N and L=CH or
(iii) L=Z=N and X=CH.

The method comprises the steps of reacting a substituted morpholineacetonitrile having the structural formula:

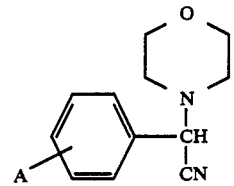

with crotononitrile and subjecting the reaction product to acid hydrolysis to obtain the corresponding 4-(substituted)-β-methyl-γ-oxobenzenebutanoic acid having the structural formula:

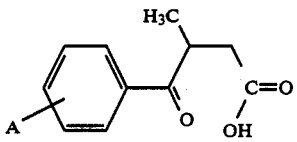

reacting the latter acid with hydrazine, and isolating the product as the free base or acid addition salt; wherein A has the above meaning.

The reaction of the morpholineacetonitrile and crotononitrile is carried out in an inert solvent, preferably THF, in the presence of a base, preferably KOH in methanol, and the reaction mixture after concentration to dryness is treated with alcoholic acid under reflux to obtain the desired 4-(substituted)-β-methyl-γ-oxobenzenebutanoic acid. The reaction of the latter acid with hydrazine, preferably as 80% hydrazine hydrate, is suitably carried out according to the invention in an alcoholic solvent at reflux temperature. The acetonitrile starting material can be obtained as the reaction product of KCN, the appropriately substituted 1-(4-phenyl)carboxaldehyde, morpholine, and p-toluenesulphonic acid in dioxane, by a procedure described in detail hereinafter. The desired final pyridazinone product can be isolated from the reaction mixture in the free base form or acid addition salt form. For formulation purposes, the product can be used as the free base or the salt form such as the sulfate, phosphate or methanesulfonate salt. Other appropriate pharamceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluenesulfonate and the like respectively.

The acid addition salts are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

In another aspect, the invention relates, as indicated, to pharmaceutical compositions for increasing cardiac contractility containing an effective amount of one or more of the 5-methylpyridazinone compounds having formula I as active components of the respective compositions for their pharmacological activity, particularly their cardiotonic and/or antihypertensive activity, and a pharmaceutically acceptable carrier.

When being utilized as cardiotonic and/or antihypertensive preparations, the pharmaceutical compositions of the invention can take any of a wide variety of oral and parenteral dosage forms. The dosage forms comprise as the active component, one or more compounds of formula I, as the free base or corresponding pharmaceutically acceptable salt.

For preparing pharmaceutical compositions, one uses inert, pharmaceutically acceptable carriers that can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier, providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable collorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 10 mg to 100 mg according to the particular application and the potency of the active ingredient.

In therapeutic use as a cardiotonic agent or an antihypertensive agent, the compositions are constituted such that the active pyridazinone content can be conveniently at the initial oral dosage of about 0.03 mg to about 10 mg per kilogram of weight. A pyridazinone content such as to give a dose range of about 0.1 mg to about 3 mg of pyridazinone per kilogram is preferred.

The pharmaceutical compositions preferably are constituted so that they can be administered parenterally or orally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitation inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit parenteral dosage form can, for example, contain the principal active compound in amounts ranging from about 0.03 to about 100 mg, with from about 0.1 to 50 mg being preferred. Expressed in proportions, the active compound is generally present in from about 0.03 to about 100 mg/ml of carrier. In the case of compositions containing supplementary active ingredients, the dosages are determined by reference to the usual dose and the manner of administration of the said ingredients. The daily parenteral doses for mammalian subjects to be treated ranges from 0.03 mg/kg to 30 mg/kg. The preferred daily dosage range is 0.1 mg/kg to 3.1 mg/kg.

The following nonlimiting examples illustrate the inventors' preferred methods for preparing the compounds of the invention.

The usefulness of the pharmaceutical compositions of the present invention as cardiotonic preparations is demonstrated by the effectiveness of the active 5-methyl pyridazinone component contained therein in standard pharmacological test prodceures. One procedure, for example, measures the effectiveness in causing a significant increase in the myocardial contractility in the pentobarbital-anesthetized dog with low or minimal changes in heart rate and blood pressure. This test procedure is described in the following paragraphs.

Test for in vivo Myocardial Inotropic Activity in Anesthetized Dog

This screen consists of determining the effects of increasing intravenous doses of compound on myocardial contractility (dP/dt max of left ventricular blood pressure), heart rate and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The treachea is intubated but the animals are permitted to breathe spontaneously. A cannula is inserted into the femoral vein for administering test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the test substance is dissolved in 0.9% saline solution or in dilute HCl or NaOH (0.1 or 1.0N) and is diluted to volume with normal saline. Ethanol or dimethylacetamide can be used as solvent if adequate dilutions can be made. Appropriate vehicle controls are administered when needed.

Each dose of the test substance is administered in a volume of 0.1 ml/kg over a period of one minute.

It is a unique feature of the present invention that the 4,5-dihydro-5-methyl-3(2H)-pyridazinone contained in the pharmaceutical compositions is outstandingly superior to corresponding desmethyl compounds with respect to cardiotonic affect. For example, when tested by the above described Anesthetized Dog Procedure, the 4,5-dihydro-5-methyl-3(2H)-pyridazinone active substance of the compositions of the present invention when administered intravenously at a rate of about 0.001 to 0.31 mg/kg/min, typically causes unexpected improvement over the corresponding desmethyl 4,5-dihydro-3(2H)-pyridazinone by a factor of about three to about ten with respect to myocardial contractility. The improvement can be seen, for example, in the following results comparing 4,5-dihydro-6-[4-(1H-imidazol-1-yl)phenyl]-5-methyl-3(2H)-pyridazinone and the corresponding desmethyl compound:

Test Results of 4,5,-dihydro-6-[4-(1H—imidazol-1-yl)phenyl]-3(2H)—pyridazinone Using Anesthetized Dog Procedure

| Dose (mg/kg) | % Change | | |
|---|---|---|---|
| | Myocardial Contractility | Heart Rate | Blood Pressure |
| 0.01 | 10.2 ± 1.3 | 0 ± 1.2 | −0.7 ± 0.4 |
| 0.03 | 37.2 ± 8.0 | 5.6 ± 3.4 | −4.1 ± 1.6 |
| 0.10 | 74.2 ± 13.3 | 6.2 ± 5.8 | −5.3 ± 1.6 |
| 0.31 | 127.3 ± 14.2 | 19.2 ± 9.1 | −13.2 ± 2.8 |
| 1.0 | 146.7 ± 25.0 | 33.8 ± 17.0 | −22.4 ± 2.8 |

Test Results of 6-[4-(1H—imidazol-1-yl)phenyl]-5-methyl-3(2H)—pyridazinone Using Anesthetized Dog Procedure

| Dose (mg/kg) | % Change | | |
|---|---|---|---|
| | Myocardial Contractility | Heart Rate | Blood Pressure |
| 0.001 | 10.5 ± 9.0 | 2.5 ± 2.1 | 2.1 ± 1.9 |
| 0.003 | 24.6 ± 4.2 | 5.6 ± 3.6 | 1.0 ± 2.1 |
| 0.01 | 50.6 ± 11.2 | 6.0 ± 5.3 | −1.7 ± 1.1 |
| 0.03 | 124.0 ± 29.4 | 25.2 ± 8.2 | −7.4 ± 1.3 |
| 0.10 | 148.5 ± 22.5 | 43.8 ± 12.0 | −19.0 ± 1.3 |
| 0.31 | 118.5 ± 31.7 | 47.5 ± 15.5 | −35.2 ± 1.3 |

Similar improvement is seen in the following results comparing 4,5-dihydro-6-[4-(4,5,6,7-tetrahydro-1H-benzimidazol-1-yl)phenyl]-5-methyl-3(2H)-pyridazinone and the corresponding desmethyl compound:

Test Results of 4,5-dihydro-6-(4,5,6,7--tetrahydro-
1H—benzimidazol-1-yl)phenyl]-3(2H)—pyridazinone Using
Anesthetized Dog Procedure

| Dose (mg/kg) | % Change | | |
|---|---|---|---|
| | Myocardial Contractility | Heart Rate | Blood Pressure |
| 0.01 | 9.3 | 1.6 | −1.1 |
| 0.03 | 28.3 | 2.3 | −3.3 |
| 0.10 | 70.3 | 3.3 | −5.3 |
| 0.31 | 136.0 | 19.3 | −11.5 |
| 1.0 | 161.0 | 31.0 | −21.0 |

Test Results of 4,5-dihydro-6-(4,5,6,7-tetrahydro-
1H—benzimidazol-1-yl)phenyl]-5-methyl-3(2H)—
pyridazinone Using Anesthetized Dog Procedure

| Dose (mg/kg) | % Change | | |
|---|---|---|---|
| | Myocardial Contractility | Heart Rate | Blood Pressure |
| 0.001 | 4 | 1 | .5 |
| 0.003 | 12 | 2 | −1.0 |
| 0.01 | 34 | 2 | −5.0 |
| 0.03 | 90 | 10 | −11.5 |
| 0.10 | 126 | 20 | −21.0 |

Preferred embodiments of the invention are illustrated by the following examples.

PREPARATION OF STARTING MATERIALS

EXAMPLE 1

1-[4-(4,5,6,7-tetrahydro-1H-benzimidazol-1-yl)phenyl]-carboxaldehyde

A mixture of 4,5,6,7-tetrahydro-1H-benzimidazole [25.6 g, 0.21 mol, prepared by following the procedure of H. Schubert and H. Fitsche, *J. Prakt. Chem* 4, (7), 407 (1958)], p-fluorobenzaldehyde (26 g, 0.21 mol) anhydrous $K_2CO_3$ (29.2 g, 0.21 mol) and CuO (300 mg) in pyridine (100 ml) is heated under reflux for 18 hours. The reaction mixture is cooled, $CH_2Cl_2$ is added and the solution is filtered. The inorganic residue is washed exhaustively with $CH_2Cl_2$. The filtrate and the washings are combined and evaporated to dryness. The residue is dissolved in $CH_2Cl_2$, filtered through silica gel and the filtrate is evaporated to give 15.5 g of the product, 1-[4-(4,5,6,7-tetrahydro-1H-benzimidazol-1-yl)phenyl]carboxaldehyde, mp 104°–105° C.

EXAMPLE 2

4-(4,5,6,7-Tetrahydro-1H-benzimidazol-1-yl)-β-methyl-γ-oxobenzenebutanoic acid

A suspension of KCN (4.4 g, 0.67 mol) in water (6 ml) is added slowly to a stirred solution of a mixture of 1-[4-(4,5,6,7-tetrahydro-1H-benzimidazol-1-yl)phenyl]-carboxaldehyde (15.2 g, 0.067 mol), morpholine (12.7 g, 0.15 mol) and p-toluenesulphonic acid (7.6 g, 0.067 mol) in dioxane (100 ml). The above mixture is heated under reflux for three hours, concentrated to a small volume and poured into water. The oil is extracted with $CH_2Cl_2$, the extract is washed with water, dried, and evaporated to yield a highly viscous gum (21.3 g) which is directly used for the next step. To a stirred solution of the above morpholineacetonitrile complex in THF (100 ml) is added a solution of 30% KOH in methanol (2 ml) followed by a slow addition of crotononitrile (5.3 g, 0.08 mol) over a period of 15 minutes. The solution is stirred overnight at room temperature followed by heating under reflux for five hours. The reaction mixture is evaporated to dryness. Toluene is added and the solution is evaporated to dryness. This procedure is repeated twice. The residue is dissolved in methanol (120 ml), 6N HCl (150 ml) is added and the mixture is heated under reflux for 17 hours. The solution is evaporated to dryness, the residue is dissolved in water and the pH is adjusted to 8.0. The gummy material which separates is removed by extraction with $CH_2Cl_2$. The aqueous solution is acidified to pH ~5.0, the crystalline material is filtered, washed with water, and finally crystallized from ethanol to give 7.8 g of 4-(4,5,6,7-tetrahydro-1H-benzimidazol-1-yl)-β-methyl-γ-oxobenzenebutanoic acid, mp 210°–211° d.

Preparation of
4,5-dihydro-5-methyl-3(2H)-pyridazinones

EXAMPLE 3

4,5-Dihydro-6-[4-(4,5,6,7-tetrahydro-1H-benzimidazol-1-yl)phenyl]-5-methyl-3(2H)-pyridazinone A mixture of 4-(4,5,6,7-tetrahydro-1H-benzimidazol-1-yl)-β-methyl-γ-oxobenzenebutanoic acid (7.3 g, 0.023 mol), 80% hydrazine hydrate (1.75 g, 0.028 mol) in ethanol (75 ml) is heated under reflux for six hours. The solution is concentrated to a small volume and filtered. The residue is washed with 2-propanol, followed by ether to give 3.1 g of 4,5-dihydro-6-[4-(4,5,6,7-tetrahydro-1H-benzimidazol-1-yl)phenyl]-5-methyl-3(2H)-pyridazinone, mp 199°–200° C.

Anal calcd for $C_{18}H_{20}ON_4$: C, 70.10; H, 6.54; N, 18.17; Found: C, 69.77; H, 6.28; N, 18.09.

EXAMPLE 4

4,5-Dihydro-6-[4-(1H-imidazol-1-yl)phenyl]-5-methyl-3(2H)-pyridazinone (4a)

A suspension of KCN (6.6 g in 8 ml of water) is added slowly to a stirred solution of a mixture of 1-[4-(1H-imidazol-1-yl)phenyl]carboxaldehyde [17.2 g, prepared by following the procedure of L. M. Sitkina and A. M. Simonov, Khim Geterotsikl. Soedin. Akad. Nauk. Latv. SSR, 1, 143 (1966)—*Chem. Abstr.* 65, 13686 (1966)] p-toluenesulfonic acid (19 g) and morpholine (11.4 g) in dioxane (100 ml). The mixture is refluxed for three hours, concentrated to half its volume and poured into saturated $K_2CO_3$ solution. The oil is extracted with $CH_2Cl_2$, the $CH_2Cl_2$ extract is washed with water, dried, and evaporated to yield an oil which is filtered through silica gel. The oil is finally crystallized from ether to give 16.1 g of the desired morpholineacetonitrile adduct, mp. 138°–139° C.

To a stirred solution of the above morpholineacetonitrile[4-(1H-imidazol-1-yl)phenyl]-4-morpholineacetonitrile (14 g) in THF (120 ml) is added 30 drops of 30% KOH in methanol followed by a slow addition of crotononitrile (4.2 g) over a period of 15 minutes. The resulting reaction mixture is stirred at room temperature for 90 minutes, the reaction mixture is concentrated in vacuo, and the residue is treated with water and the oil is extracted with $CH_2CL_2$. The extract is washed with water, dried, and concentrated. The resulting viscous gum is dissolved in 30 ml of 6N HCl, heated on a steam bath for six hours, and the reddish solution is evaporated to dryness in vacuo. The residue is dissolved in water and pH is adjusted to 8.0. The gummy material is removed by extraction with $CH_2Cl_2$ and the aqueous solution is acidified to pH 5.0. The crystalline material is filtered, washed with water, and finally crystallized from 2-propanol to give 10.4 g of 4-(1H-imidazol-1-yl)-β-methyl-γ-oxobenzenebutanoic acid, mp 181°–182° C.

An ethanolic solution (60 ml) of the above acid (10.4 g) containing 85% hydrazine hydrate (2.5 ml) is heated under reflux for four hours. The solution is cooled, diluted with water, and filtered. The solid is crystallized from ethanol/tetrahydrofuran to yield 7.6 g of the product, 4,5-dihydro-6-[4-(1H-imidazol-1-yl)phenyl]-5-methyl-3(2H)-pyridazinone, mp 197°–198° C.

Anal calcd for $C_{24}H_{24}N_4O$: C, 66.12; H, 5.55; N, 22.04; Found: C, 66.12; H, 5.54; N, 21.95.

Hydrochloric acid-addition salt of 4,5-dihydro-6-[4-(1H-imidazol-1-yl)phenyl]-5-methyl-3(2H)-pyridazinone is prepared by adding an ethanolic solution of hydrochloric acid to a hot solution of 70 g of 4,5-dihydro-6-[4-(1H-imidazol-1-yl)phenyl]-5-methyl-3(2H)-pyridazinone in about 1400 ml of ethanol to a pH of about 2.0, chilling the mixture and collecting the precipitated salt, 78 g, mp 296°–298° d.

Anal calcd for $C_{14}H_{14}N_4O$, HCl: C, 57.83; H, 5.20; N, 19.27; Found: C, 57.99; H, 5.07; N, 19.30.

Similarly, by following the above procedure, one obtains the following compounds.

4,5-Dihydro-6-[4-(2-ethyl-4-methyl-1H-imidazol-1-yl)phenyl]-5-methyl-3(2H)-pyridazinone (4b)
4,5-Dihydro-6-[4-(2-methyl-1H-imidazol-1-yl)phenyl]-5-methyl-3(2H)-pyridazinone (4c)
4,5-Dihydro-6-[4-(4-hydroxymethyl-1H-imidazol-1-yl)phenyl]-5-methyl-3(2H)-pyridazinone (4d)
4,5-Dihydro-6-[4-(1H-benzimidazol-1-yl)phenyl]-5-methyl-3(2H)-pyridazinone (4e)
4,5-Dihydro-6-[4-(1H-1,2,4-triazol-1-yl)phenyl-5-methyl-3(2H)-pyridazinone (4f)
4,5-Dihydro-6-[4-[2-(1H-imidazol-1-yl)ethoxy]phenyl]-5-methyl-3(2H)-pyridazinone (4g)
4,5-Dihydro-6-[4-[2-(1H-imidazol-1-yl)ethyl]phenyl]-5-methyl-3(2H)-pyridazinone (4h)
4,5-Dihydro-6-[4-(1H-imidazol-1-yl-methyl)phenyl]-5-methyl-3(2H)-pyridazinone (4i)

The following representative Examples A through D, are given as illustrative pharmaceutical compositions utilizing different carriers. In these Examples, Example A illustrates the use of the compounds of the invention in injectables suitable for intravenous or other types of injection into the host animal. Example B is directed to an oral syrup preparation, Example C to an oral capsule preparation, and Example D to oral tablets. In each of Examples A through D, the ingredients are first listed and are then followed by the method of preparing the composition.

EXAMPLE A

INJECTABLES

| | |
|---|---|
| Product of Example 4a | 125 mg–500 mg |
| Water for Injection USP q.s. | |

The hydrochloride salt of the product of Example 4a, 4,5-dihydro-6-[4-(1H-inidazol1-yl)phenyl]-5-methyl-3(2H)-pyridazinone, is dissolved in the water and passed through a 0.22 micron filter. Aliquots of the filtered solution is added to ampoules or vials, sealed and sterilized. A similar injectable formulation is made by this procedure in which the Example 4 product is replaced by an equal quantity of the hydrochloride salt of 4,5-dihydro-6-[4-[2-(1H-imidazol-1-yl)ethoxy]phenyl]-5-methyl-3(2H)-pyridazinone (compound 4g).

EXAMPLE B

SYRUP

| 250 mg Active ingredient/5 ml syrup | |
|---|---|
| COMPOUND 3 | 25 g |
| Purified Water USP | 200 ml |
| Cherry Syrup q.s. or | 1000 ml |

COMPOUND 3, 4,5-dihydro-6-[4-(4,5,6,7-tetrahydro-1H-benzimidazol-1-yl)phenyl]-5-methyl-3(2H)-pyridazinone hydrochloride, is dissolved in the water and to this solution the syrup is added with mild stirring.

EXAMPLE C

CAPSULES

| 50 mg, 125 mg or 250 mg | |
|---|---|
| COMPOUND 4b | 500 g |
| Lactose USP, Anhydrous q.s. or | 200 g |
| Sterotex Powder HM | 5 g |

Combined COMPOUND 4b, 4,5-dihydro-6-[4-(2-ethyl-4-methyl-1H-imidazol-1-yl)phenyl]-5-methyl-3(2H)-pyridazinone, and the Lactose in a Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg. 352.5 mg or 705 mg of the blend, respectively, for the 50 mg, 125 mg, and 250 mg containing capsules.

EXAMPLE D

TABLETS

| 50 mg, 100 mg or 250 mg | |
|---|---|
| COMPOUND 4f | 250 g |
| Corn Starch NF | 200.0 g |
| Cellullose, Microcrystalline | 46.0 g |
| Sterotex Powder HM | 4.0 g |
| Purified Water q.s. or | 300.0 ml |

Combined the corn starch, the cellulose and Compound 4f, 4,5-dihydro-6-[4-(1H-1,2,4-triazol-1-yl)phenyl]-5-methyl-3(2H)-pyridazinone, together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total belnded for five minutes by drum rolling. Compressed tablets of 150 mg, 375 mg, and 750 mg respectively, of the toal mix are formed with appropriate sized punches for the 50 mg, 125 mg, or 500 mg containing tablets.

The embodiments of the invention in which an exclusive property or privilege is claimed are defined as follows:

1. A pharmaceutical composition for increasing cardiac contractility comprising an effective amount of 4,5-dihydro-6-[4-(1H)-imidazol-1-yl)phenyl]-5-methyl-3(2H)-pyridazinone or a pharmaceutically acceptable salt thereof, and a pharmaceutically acceptable carrier.

2. A pharmaceutical composition for increasing cardiac contractility comprising an effective amount of 4,5-dihydro-6-(4,5,6,7-tetrahydro-1H-benzamidizol-1-yl)phenyl)-5-methyl-3(2H)-pyridazinone or a pharmaceutically acceptable salt thereof, and a pharmaceutically acceptable carrier.

* * * * *